(12) United States Patent
Matusch

(10) Patent No.: US 8,287,493 B2
(45) Date of Patent: Oct. 16, 2012

(54) DISPOSABLE INJECTOR COMPRISING AT LEAST ONE DRAW HOOK AND A SLIDING WEDGE-TYPE GEAR FOR UNLOCKING A LOCKING ELEMENT

(75) Inventor: Rudolf Matusch, Marburg (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 0 days.

(21) Appl. No.: 13/405,255

(22) Filed: Feb. 25, 2012

(65) Prior Publication Data

US 2012/0197186 A1    Aug. 2, 2012

Related U.S. Application Data

(60) Division of application No. 12/587,684, filed on Oct. 10, 2009, now Pat. No. 8,167,840, which is a continuation-in-part of application No. PCT/EP2008/002391, filed on Mar. 27, 2008.

(30) Foreign Application Priority Data

Apr. 19, 2007   (DE) .................... 10 2007 018 868

(51) Int. Cl.
*A61M 5/20* (2006.01)
(52) U.S. Cl. ........................................ 604/135; 604/134
(58) Field of Classification Search .......... 604/134–137, 604/187
See application file for complete search history.

(56) References Cited

U.S. PATENT DOCUMENTS

| 4,553,962 A | 11/1985 | Brunet |
| 5,358,489 A | 10/1994 | Wyrick |
| 2006/0224124 A1 | 10/2006 | Scherer |

FOREIGN PATENT DOCUMENTS

| CA | 2 356 614 A1 | 4/2000 |
| DE | 36 44 984 A1 | 7/1988 |
| DE | 10 2004 060 146 A1 | 8/2005 |
| GB | 2 404 865 A | 2/2005 |
| WO | WO 2006/088513 A1 | 8/2006 |
| WO | WO 2008/089886 A1 | 7/2008 |

*Primary Examiner* — Kevin C Sirmons
*Assistant Examiner* — Emily Schmidt
(74) *Attorney, Agent, or Firm* — R. S. Lombard; K. Bach

(57) ABSTRACT

A disposable injector with a housing (10) in which are arranged at least one mechanical spring energy store (50), at least one cylinder-piston unit that can be filled at least temporarily with an active substance, at least one piston actuation plunger (60) and at least one triggering unit (80). The spring energy store comprises at least one pre-loaded spring element. The spring-loaded piston actuation plunger has at least one traction rod (61) which can be moved transversely, at least in certain regions, and by means of a supporting portion supports the tensioned spring energy store on at least one resting surface (37) of the housing. An actuatable triggering slide device (82) unlocks the disposable injector and releases the supporting portion to allow it to move away from the resting surface.

2 Claims, 6 Drawing Sheets

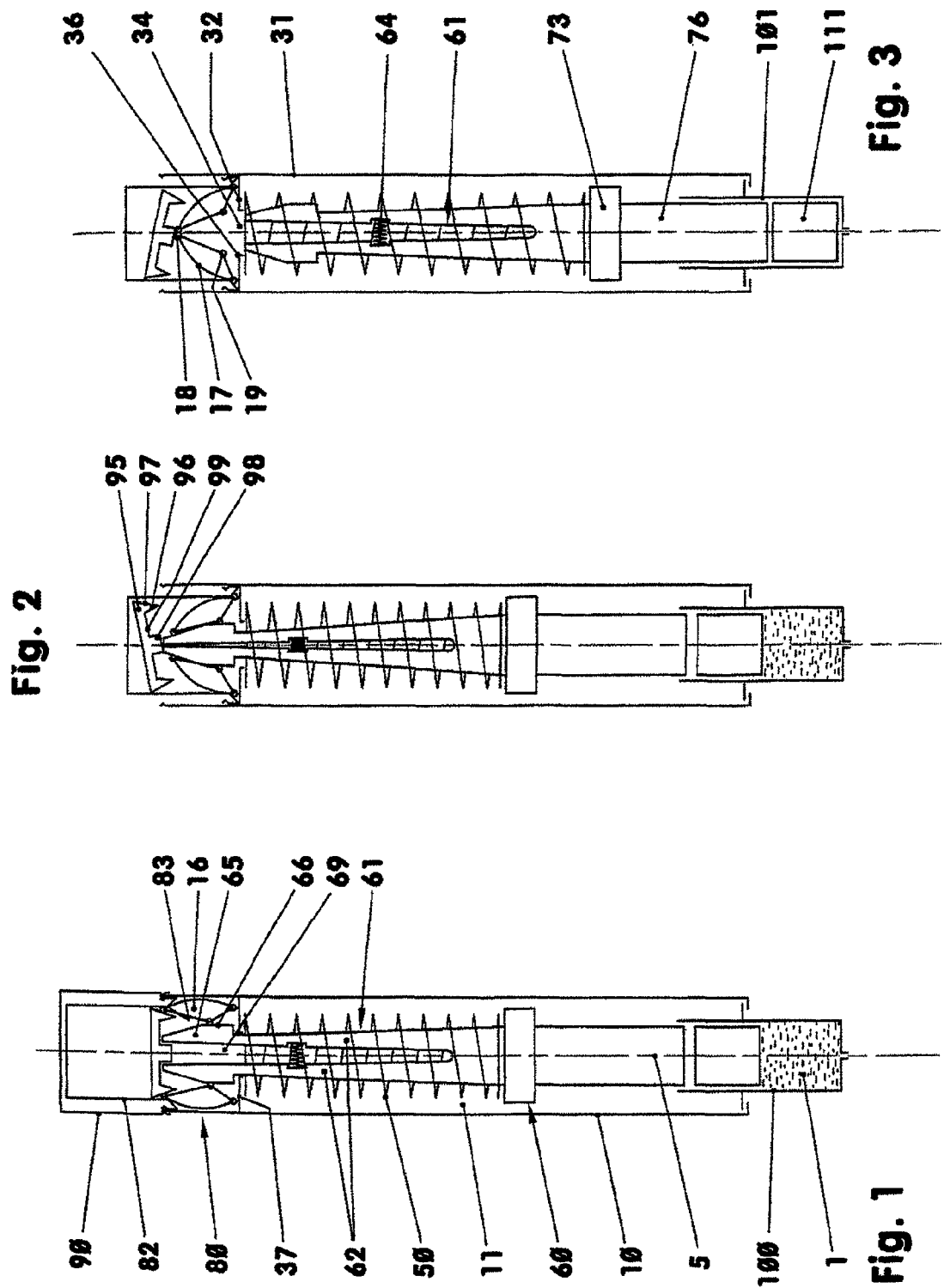

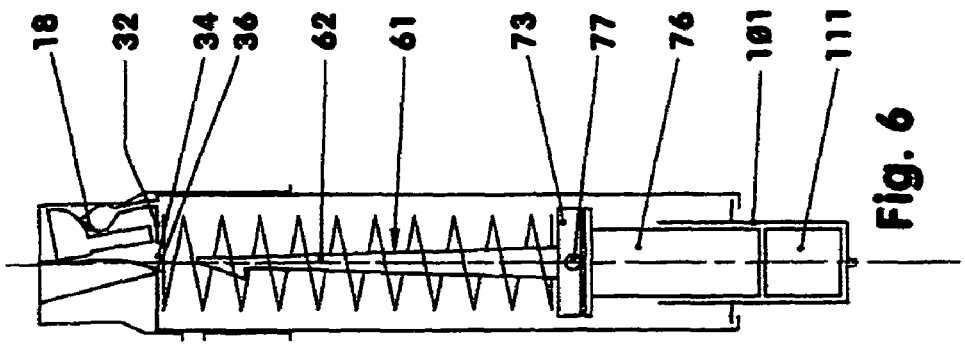
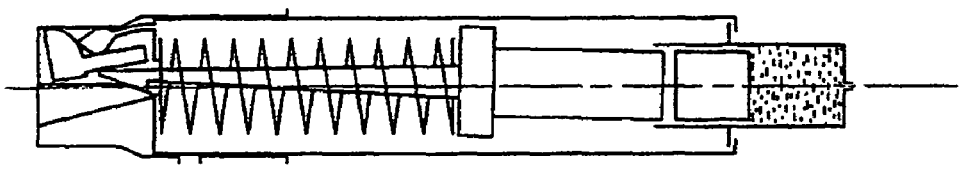
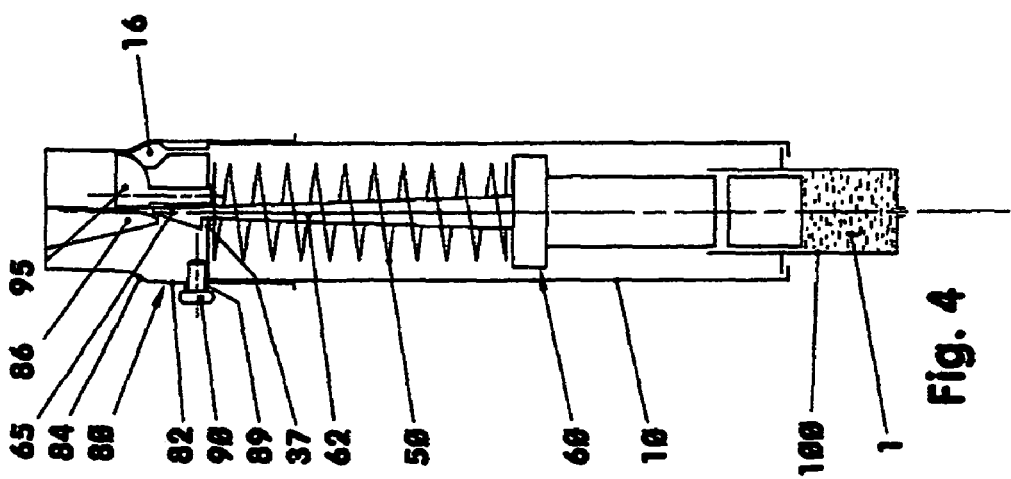

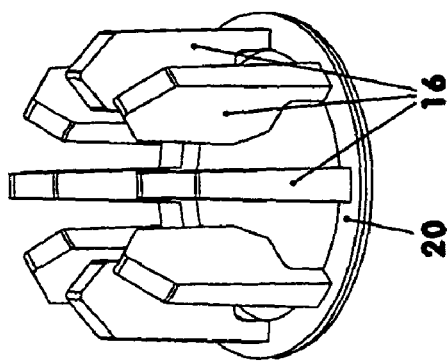
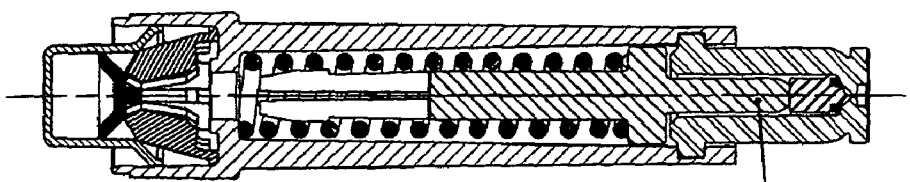
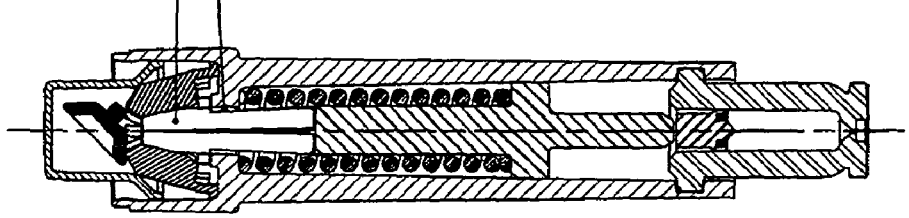
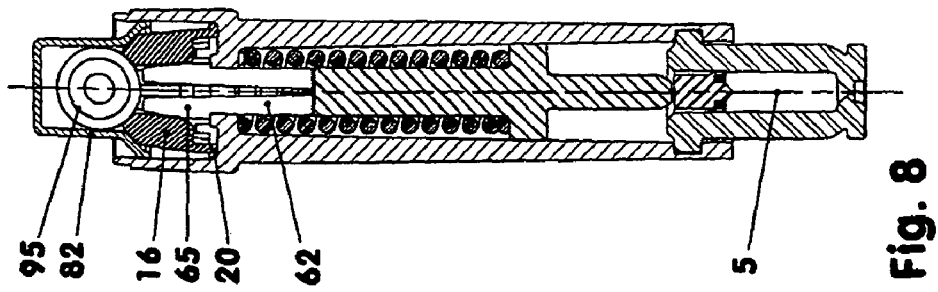

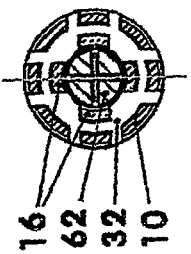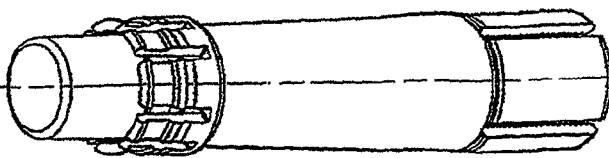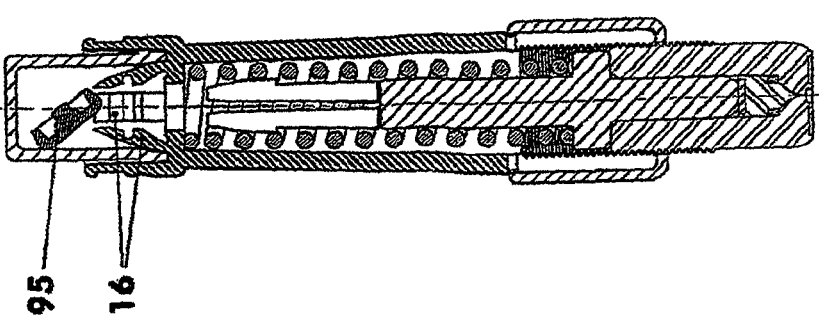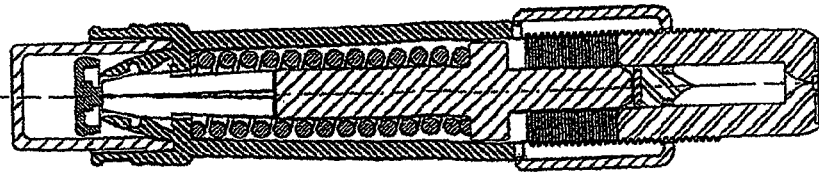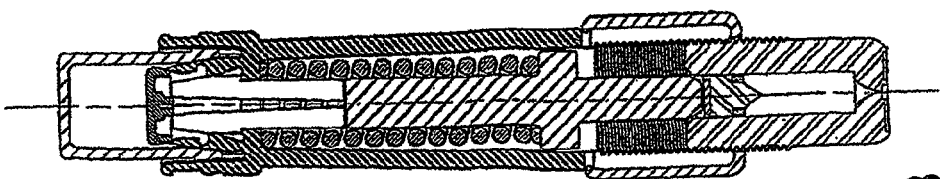

DISPOSABLE INJECTOR COMPRISING AT LEAST ONE DRAW HOOK AND A SLIDING WEDGE-TYPE GEAR FOR UNLOCKING A LOCKING ELEMENT

CROSS-REFERENCE TO RELATED APPLICATION

This application is a divisional of and claims the benefit of U.S. patent application Ser. No. 12/587,684 filed Oct. 10, 2009 now issued as U.S. Pat. No. 8,167,840, which application is incorporated herein by reference in its entirety. The said U.S. patent application Ser. No. 12/587,684 is a continuation-in-part application of pending international application PCT/EP2008/002391 filed Mar. 27, 2008 and claiming the priority of German Application No. 10 2007 018 868.6 filed Apr. 19, 2007.

BACKGROUND OF THE INVENTION

The invention relates to a disposable injector with a housing in which or on which are arranged, in each case at least in some areas, at least one mechanical spring energy reservoir, at least one cylinder/piston unit that can be filled at least temporarily with active substance, at least one piston-actuating ram and at least one trigger unit, in which the spring energy reservoir comprises at least one pretensioned spring element, in which at least part of the piston-actuating ram is positioned between the spring energy reservoir and the piston of the cylinder/piston unit, and in which the spring-loaded piston-actuating ram has at least one tension bar which is transversely movable at least in some areas and which, by means of a support portion, supports the tensioned spring energy reservoir on at least one bearing surface of the housing.

DE 36 44 984 A1 discloses an automatic injection device which is equipped with an injection needle and in which the injection needle is driven out by means of a mechanical spring reservoir and, at the same time, the injectable substance stored in the device is discharged. The spring element pretensioned in the spring reservoir is held in the housing of the injection device in the above-described manner. However, the tension bar is secured by means of a button-shaped catch element that is to be removed separately counter to the triggering direction.

The object of present invention is providing a disposable injector of modular design which, with a small overall size, comprises only a small number of components and, while being easy to handle, ensures safe storage and reliable operation.

SUMMARY OF THE INVENTION

The invention relates to a disposable injector with a housing (10) in which are arranged at least one mechanical spring energy store (50), at least one cylinder-piston unit that can be filled at least temporarily with an active substance, at least one piston actuation plunger (60) and at least one triggering unit (80). The spring energy store comprises at least one preloaded spring element. The spring-loaded piston actuation plunger has at least one traction rod (61) which can be moved transversely, at least in certain regions, and by means of a supporting portion supports the tensioned spring energy store on at least one resting surface (37) of the housing. An actuatable triggering slide device (82) unlocks the disposable injector and releases the supporting portion to allow it to move away from the resting surface.

For this purpose, the trigger unit has at least one trigger slide, at least one trigger lever bearing on the housing, and a catch element that holds the tension bar in the locked position. The trigger lever or trigger levers can be displaced by a sliding movement or pivoting movement of the trigger slide in such a way that the catch element releases the tension bar and slides the support portion from the bearing surface.

With the invention, a needleless disposable injector is made available whose piston-actuating ram or parts thereof, upon triggering of the disposable injector, executes a movement that is oriented transversely with respect to the longitudinal direction and/or transversely with respect to the centre line of the disposable injector. For pretensioning and holding the spring energy reservoir, one or more parts of the piston-actuating ram bear with at least one enclosure or a hook on the housing or on a structural part arranged on the housing. To trigger the disposable injector, the enclosures or hooks, after automatic safety release, are pushed down from their bearing surface on the housing, such that the piston-actuating ram, under the effect of the spring energy reservoir, can move at least approximately parallel to the centre line of the disposable injector.

The longitudinal movement of the triggering component derived from a press-button can also take place by means of a rotation movement relative to the injector housing. For this purpose, the triggering component is mounted in the injector housing by way of a screw thread. The screw thread and this component have a centre line that is congruent with the centre line of the injector housing. By means of a suitable rotation movement, the triggering component is moved into the injector housing. This results in the longitudinal movement necessary for the safety release and triggering.

The movement required for the safety release and triggering can also be a pure pivoting movement. For this purpose, a cam or eccentric structure can be formed integrally on the inside wall of the triggering component and, by means of the pivoting or rotation of the triggering component, moves certain elements, e.g. trigger levers of the trigger unit.

BRIEF DESCRIPTION OF THE DRAWINGS

Further details of the invention will become clear from the following illustrative embodiments represented schematically in the drawings, in which:

FIG. 1 shows a disposable injector with a tension bar;
FIG. 2 shows the same as FIG. 1, but released and actuated;
FIG. 3 shows the same as FIG. 2, but after the medicament has been expelled;
FIG. 4 shows a disposable injector with an eccentric tension bar;
FIG. 5 shows the same as FIG. 4, but released and actuated;
FIG. 6 shows the same as FIG. 5, but after the medicament has been expelled;
FIG. 8 shows the same as FIG. 7, but after the catch element has been released;
FIG. 9 shows the same as FIG. 8, but actuated;
FIG. 10 shows the same as FIG. 9, but after the medicament has been expelled;
FIG. 11 shows a separate ring with trigger levers formed integrally thereon;
FIG. 13 shows the same as FIG. 12, but after the catch element has been released;
FIG. 14 shows the same as FIG. 13, but actuated;

FIG. 15 shows the same as FIG. 14, but after the medicament has been expelled;

FIG. 16 shows a perspective view of the housing without safety cap, support sleeve and cylinder/piston unit;

FIG. 17 shows a cross section of the housing in the trigger area;

DETAILED DESCRIPTION OF THE PARTICULAR EMBODIMENTS

Figure 7:
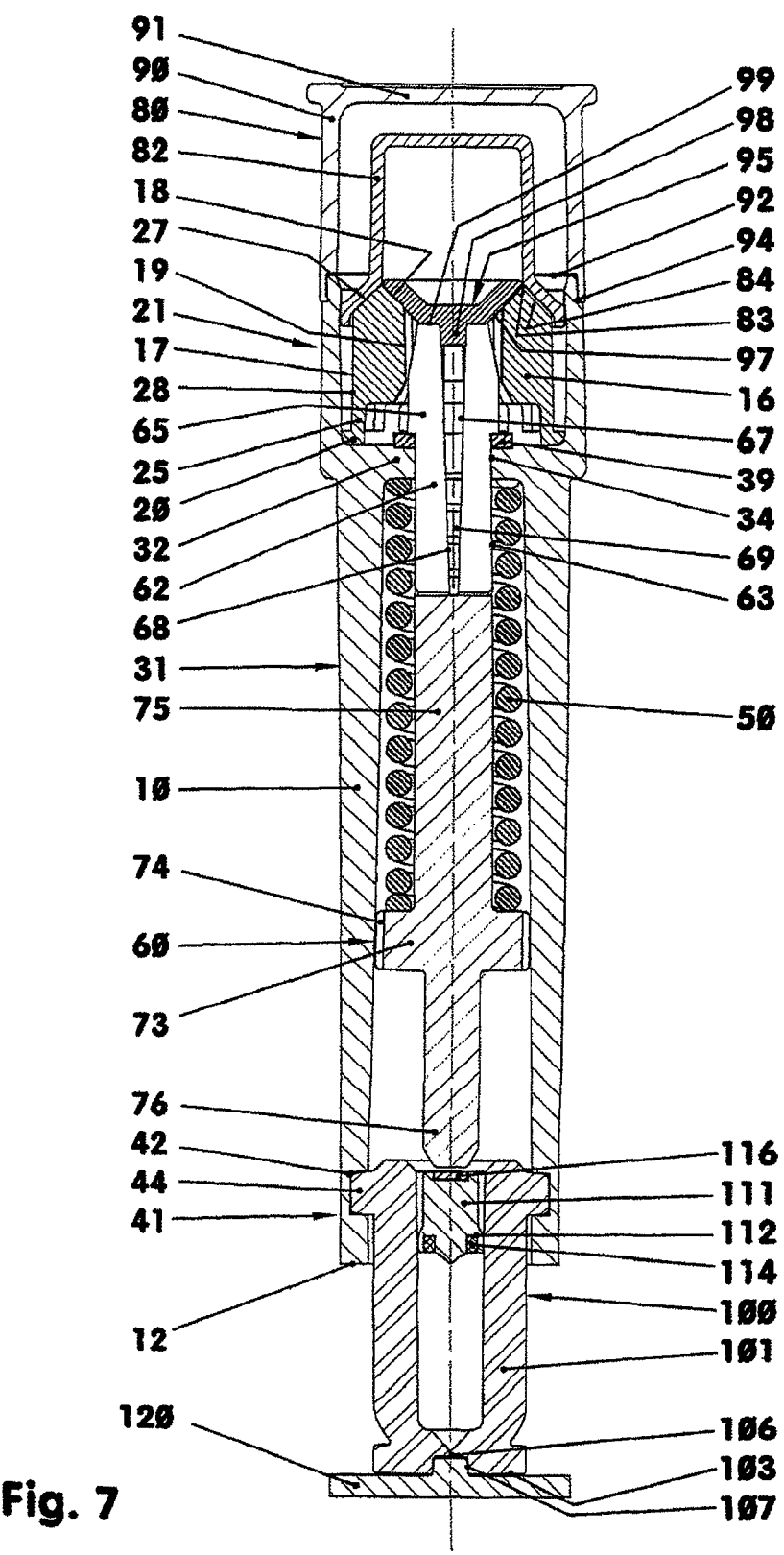
FIG. 7 shows a disposable injector with separate trigger levers.
Figure 18:
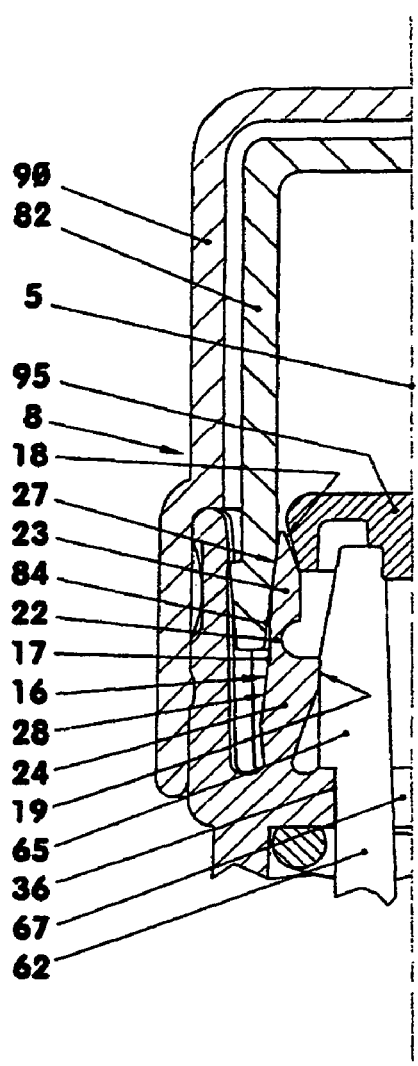
FIG. 18 shows a detail from FIG. 12.
Figure 12:
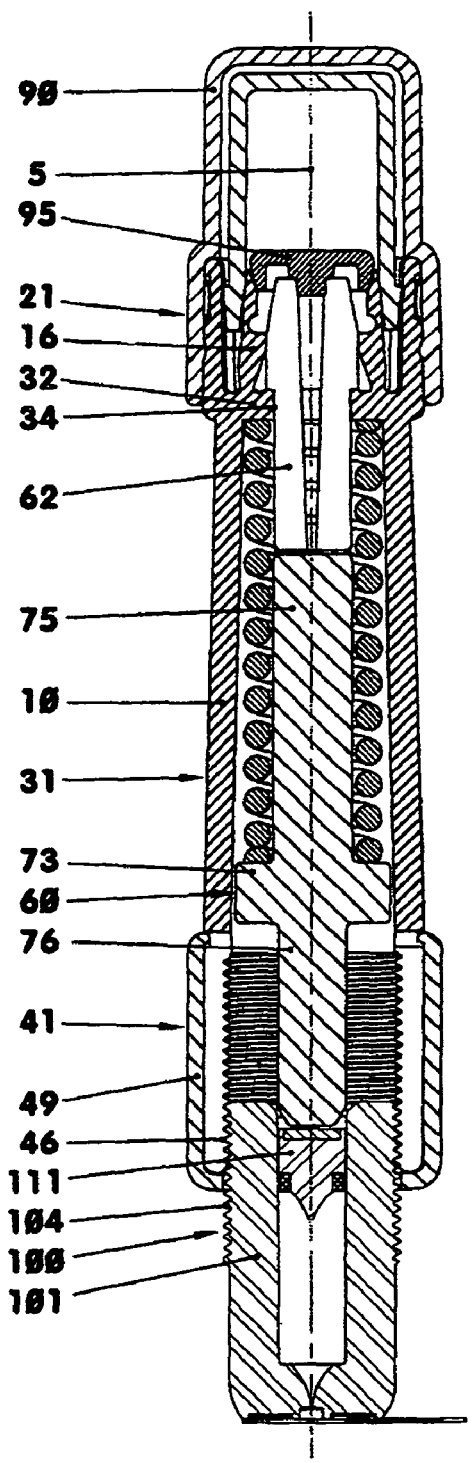
FIG. 12 shows a disposable injector with trigger levers formed integrally on the housing.

FIGS. 1 to 3 show the simplified principle of a disposable injector with a permanently charged spring energy reservoir. The disposable injector comprises a housing (10), a for example filled cylinder/piston unit (100), a piston-actuating ram (60) with a tension bar (61), and a helical compression spring (50) as spring reservoir. The tension bar (61) comprises multiply slit tension hooks (62). In addition, a trigger unit (80), in which a trigger element (82) and a safety cap (90) are arranged, sits on the housing (10).

The housing is a pot-shaped hollow body open at the top and bottom and with an intermediate base (32). The intermediate base (32) has, for example, a central opening (34) through which, according to FIG. 1, the tension hooks (62) is engaged. The individual tension hooks (62) lie with their support portions (65) on the bearing surface (37) of the housing (10).

The piston-actuating ram (60) is divided into three areas. The lower area is the piston slide (76). Its diameter is slightly smaller than the internal diameter of the cylinder (101) of the cylinder/piston unit (100). The lower end face of the piston slide (76) acts directly on the piston (111).

The middle area is the ram plate (73). The ram plate (73) is a flat and in at least some areas cylindrical disc whose external diameter is a few tenths of a millimeter smaller than the internal diameter of the housing (10) in the jacket area (31).

The upper area is the tension bar (61) consisting, for example, of two elastic tensions hooks (62) lying opposite each other. Both tension hooks (62) lie back to back and seek to force themselves apart in the manner of a leaf spring, such that they bear on the edge (36) of the opening (34) with pretensioning, for example. Their spring direction is symbolized by a helical compression spring (64) lying transversely between them as an alternative.

Of course, such a helical compression spring (64) can also really be used if, for example, the tension hooks (62) are articulated on the ram plate (73) by means of pivot hinges. The pivot axes of these pivot hinges would then lie transverse to the centre line (5) of the housing and perpendicular to the plane of the drawing according to FIGS. 1 to 3.

The cylinder/piston unit (100) is secured in the lower part of the housing (10). The cylinder/piston unit (100) here consists of a cylinder (101) which is filled with an injection solution (1) and in which a piston (111) lies in the rear position. Above the piston (111), the piston-actuating ram (60) is arranged in the housing (10) in such a way that, for example, although not touching the piston, it is laterally guided with its lower end in the upper area of the cylinder (101).

The helical compression spring (50) sits pretensioned between the ram plate (73) and the intermediate base (32) of the housing (10).

The trigger unit (80), with a trigger slide (82), several trigger levers (16) and a catch element (95), sits in the upper area of the housing (10), under a safety cap (90).

The catch element (95) is a plate-shaped rotary part with a central catch pin (98). The catch element (95) has an edge (96) that extends in the same direction as the catch pin (98). The edge (96) has a frustoconical outer wall (97) whose theoretical peak lies in front of the central catch pin. The peak angle of the outer wall (97) lies between 25 and 100 angle degrees. Of course, in the case of two or four tension hooks (62), the catch element can also be a square or polygonal plate whose outer wall has the shape of a truncated pyramid. In this case, the catch pin (98) also has a rectangular cross section.

According to FIG. 1 (see also FIG. 2), the catch element (95) bears on the tension hook (62), with the catch pin (98) being securely clamped in the upper area of the slit (69) located between the tension hooks (62). The catch pin (98) here has a rectangular cross section, for example. It blocks the tension hooks (62) mechanically in their locked position.

The trigger levers (16) arranged in the trigger area bear with their upper contact zones (18) on the opposite areas of the outer wall (97) of the catch element (95). If appropriate, the lower contact zones (19) of the trigger levers (16) at the same time touch the upper outer contour (66) of the tension hooks (62). Moreover, the pot-shaped trigger slide (82) bears on the trigger levers (16) mounted on the intermediate base. The trigger slide (82) is initially locked with a form fit in the area of the upper edge of the housing (10). It bears with an inner edge (83) on the respective outer contour (17) of the individual trigger levers (16).

If appropriate, the trigger levers (16) can be secured on a ring-shaped component (20), see FIG. 7. This component (20) then lies for example on the intermediate base (32). The trigger levers (16) protrude upwards from it. The portions of the ring-shaped component (20) that are located between two respective trigger levers can serve, inter alia, as torsion spring.

The outer contour (17) and the contact zones (18, 19) have in general a spherical curvature. However, surfaces (17-19) are also conceivable that have a flat or plane configuration at least in some areas.

The trigger slide (82), which is mounted on the upper end of the housing (10) in such a way as to be initially locked and longitudinally displaceable, bears in a sliding manner on the for example cylindrical inner surface of the trigger area of the housing (10).

To release the disposable injector, the safety cap (90), see FIG. 1, is removed from the housing (10). The disposable injector is then placed on the injection site. To trigger it, a finger of the hand holding the disposable injector is used to press the trigger slide (82), like a press-button, linearly into the housing (10). The inner edge (83) of the trigger slide (82) presses the trigger levers (16) with the upper contact zone (18) against the outer wall (97) of the catch element (95) via their outer contour. The catch element (95) is pressed upwards, as a result of which the catch pin (98) springs from the slit (69), counter to the direction of movement of the trigger slide (82). At the same time, or also slightly later, the lower contact zone (19) comes to rest on the outer contour (66) of the tension hooks (62). By means of the increasing pivoting of the trigger levers (16), under the thrust of the trigger slide (82), the support portions (65) of the tension hooks (62) are bent towards the centre line (5) counter to the action of the spring element (64). As a result, the support portion (65), under the effect of the helical compression spring (50), slips through the opening (34) into the interior (11) of the housing (10). In this process, the cylinder/piston unit (100) is emptied, see FIG. 3.

As soon as the for example elastically deformed tension hooks (62) as parts of the piston-actuating ram (60) have reached the interior (11) of the housing (10), they spring away from one another again, for example.

The nature of the triggering operation is not restricted to the variant described here. Instead of the longitudinally displaceable trigger slide (82), it is possible, for example, to use an eccentric gear, a screw gear or another lever gear.

FIGS. 4 to 6 show the design plans of a disposable injector that has an eccentric hook-shaped tension bar (62). The latter passes through an eccentric opening (34) of the base (32). The tension bar (62) lies with its support portion (65) on the bearing surface (37). A trigger lever (16) extends upwards from the base (32).

The cap-shaped trigger element (82) sits longitudinally displaceably on the housing (10). The trigger element (82) has a conical, frustoconical or pyramidal area (84) and additionally carries in its interior a trigger wedge (86). Its wall has a recess (89) in which, according to FIG. 4, a for example mushroom-shaped safety element (90) is optionally arranged. The safety element (90) rests on the bearing surface (37).

Between the tension bar (62) and the trigger lever (16), a catch element (95) is located in the trigger unit (80). It bears at the left-hand side on the trigger wedge (86) and at the right-hand side on the upper contact zone (18) of the trigger lever (16). At the same time, a part of the catch element (95) sits in the recess (34), blocking the tension bar (62).

To release the disposable injector, the safety element (90) is first of all pulled out of the trigger element (82). The disposable injector is then triggered by pressing the trigger element (82) down in the manner of a press-button. The trigger element (82) slides along the outer wall of the housing (10). In doing so, the area (84) first contacts the trigger lever (16) and presses the latter via the contact zone (16) against the catch element (95). The latter deflects upwards and frees the recess (34). The trigger wedge (86) then rests on the support portion (65) of the tension bar (62) and pushes it into the recesses (34), see FIG. 5. The piston-actuating ram (60) released in this way shoots downwards and in doing so empties the cylinder/piston unit (100).

In this principle, and in the other principles shown here, the piston-actuating ram (60) can have a separate piston slide (76). For this purpose, it is then guided on the inside wall of the housing (10) and/or is mounted on the ram plate (73) by a hinge (77), see FIG. 6.

It is also possible to form the piston slide (76) as piston rod integrally on the piston (111) and thus to guide the piston rod only by the piston (111) and/or by contact, in some areas for example, on the inside wall of the cylinder (101). Of course, the piston slide (76) and the piston rod can share the space between the ram plate (73) and the piston (111) in any desired way.

FIGS. 7 to 11 show an embodiment of the principle described in FIGS. 1 to 3. Here, the supporting component is the housing (10). It has a substantially tubular shape and is divided into three functional areas (21, 31, 41). According to FIG. 7, the upper area is the trigger area (21). This is adjoined by the jacket area (31). An intermediate base (32) is arranged between the two areas and also protrudes slightly radially beyond the jacket area (31). The intermediate base (32) has a central recess (34), the diameter of which widens slightly, for example towards the bottom.

In the trigger area (21) of the housing (10), a dimensionally rigid, for example metal, apertured disc is located on the intermediate base (32), and in this case it is for example countersunk around the bore (34). It is adhesively bonded or injection-moulded therein. The apertured disc (39) protects the intermediate base (32) from pressures and/or other deformations. It also prevents sticking of the components (32) and (65) that are otherwise in contact there.

The fixing area (41) for receiving the insertable cylinder/piston unit (100) is arranged below the jacket area (31). The unslotted fixing area (41) is part of a bayonet catch. For this purpose, two or more angled channels (42) are arranged on its inner wall. The channels (42) lead vertically upwards from the lower end face (12) of the housing and, after a length of a few millimeters, each merge into a short horizontal channel portion.

In the fixing area (41), the cylinder (101) is fitted and fixed via two or more bayonet pins (44). If appropriate, one or more locking elements, that prevent detachment of the bayonet catch, i.e. removal of the cylinder (101), are located in the horizontal channel portion or on at least some of the bayonet pins (44).

The cylinder (101) is a thick-walled pot, for example. The rodless piston (111) sits in the for example cylindrical bore of the cylinder (101). At its front end face, of at least approximately conical configuration, the piston (111) has an axial annular groove (112) for receiving a sealing ring (114) or a permanently elastic sealing compound. A for example cylindrical metal plate (116) is let into the rear end face of the piston (111).

A short cylindrical, nozzle-like bore (106) is located at the centre of the bore of the cylinder (101), whose cylinder base is adapted at least approximately to the contour of the front end face of the piston. The diameter of the bore (106) is approximately 0.1 to 0.5 millimeter. This bore (106) is one to five times as long as its diameter. It ends in a cylindrical recess (107) of the outer end face (103) at the bottom of the cylinder (101).

The spring energy reservoir (50) or the drive unit of the disposable injector is arranged between the piston (111) and the trigger area (21). The spring energy reservoir (50) is a helical compression spring arranged on a piston-actuating ram (60) with four tension hooks (62). By means of the support portions (65) of the tension hooks (62), the helical compression spring (50) sits tensioned in the housing (10). It is supported between the inside face of the intermediate base (32) and an upper end face of the piston-actuating ram (60).

The piston-actuating ram (60) is divided into three areas. The lower area is the piston slide (76), the middle area is the ram plate (73) bearing the spring element (50), and the upper area is a for example cylindrical portion (75) adjoined by the bundle of for example four tension hooks (62). In the jacket area (31) of the housing (10), the portion (75) and the bundle of tension hooks (62) have at least approximately a cylindrical envelope surface (63), i.e. their outer walls have the curvature of a cylinder jacket area. The diameter of the envelope surface (63) is smaller than the smallest diameter of the spring element (50).

As envelope surface, the support portion (65) here has in some areas a frustoconical jacket and in some areas a cylinder. Both areas are the same length, for example.

The inner walls of the tension hooks (62) are parts of an envelope surface (68) having the shape of a frustoconical jacket. This envelope surface (68) encloses the frustoconical jacket-shaped hollow space (67) located between the tension hooks. The cross sections of the hollow space (67) increase the further they are from the portion (75). The radial slits (69) lying between adjacent tension hooks (62) increase in size towards the top, according to FIG. 7, to approximately three times the width.

The ram plate (73) according to FIG. 7 has, for example, two grooves (74) lying opposite each other.

The tension hooks (62) fit with their support portions (65) in the trigger area (21). The support portions (65) lie secured on the intermediate base (32).

In the trigger area (21), a trigger slide (82) sits as part of a trigger unit (80) in its upper position under a safety cap (90). The trigger slide (82) is a pot-shaped body whose front area widens in a funnel shape. The cone angle of this area measures, for example, 90 angle degrees. The inner wall of the funnel-shaped area serves as a slide surface (84), which ends at a so-called inner edge (83). There, the slide surface (84) merges into an at least approximately cylindrical area. The size of the hollow space of the cylindrical area is chosen such that the catch element (95) fits in it in any desired position and in each trigger position of the trigger slide (82).

The trigger slide (82) lies with its slide surface (84) on a group of eight trigger levers (16). The trigger levers (16) are formed integrally on a ring (20), see FIG. 11. The ring (20) lies loosely on the intermediate base (32), according to FIG. 7. If appropriate, it can also be clamped securely and/or locked on the housing (10). The ring (20) is at least supported on the at least approximately cylindrical inner wall of the trigger area (21).

Here, the individual trigger levers (16) are narrow, for example hexagonal plates, which are arranged on the ring (20) via a foot (25). The trigger levers (16) have a two-part outer contour (17). According to FIG. 7, the upper part (27) lies on the slide surface (84). The lower part (28) extends in a straight line, for example, approximately parallel to the inner wall of the trigger area (21). This part (28) of the outer contour (17) ends on the ring (20).

Facing the centre line (5), each trigger lever (16) has two active zones. These are an upper contact zone (18) and a lower contact zone (19). According to FIG. 7, the upper contact zone (18) is inclined by 45 angle degrees relative to the centre line (5). It contacts the catch element (95) on the frustoconical outer wall (97) of the latter. The lower contact zone (19) forms an angle of approximately one angle degree with the centre line (5). According to FIG. 7, this zone has no contact with the tension hooks (62).

The outer contour parts (27, 28) and the contact zones (18, 19) are each, for example, subsidiary surfaces of conical or cylindrical jackets. The centre lines of these jackets are congruent with the centre line (5).

The division of the trigger levers (16) sitting on the ring (20) is chosen such that none of the trigger levers (16) can move into one of the slits (69) during the triggering procedure. If appropriate, this is also ensured by a particular shaping of the slit (69) or of the trigger levers (16).

The catch element (95), resting according to FIG. 7 on the trigger levers (16), has a funnel-shaped configuration. Like the trigger slide (82), the catch element (95) is a rotationally symmetrical component. It consists of a plate with a central catch pin (98). The catch pin (98) engages in the upper area of the hollow space (67) located between the tension hooks (62). The plate has, on its underside, a support surface (99) with which it bears on the upper ends of the tension hooks (62).

The safety cap (90), which closes the upper end of the housing (10) and protects the trigger slide (82) from unwanted actuation, also has a pot-shaped configuration. It has an almost flat base (91), which all the way round protrudes slightly beyond the side wall of the safety cap (90), such that the cap (90) can also be flipped away by the thumb of the hand holding the disposable injector—in the context of one-handed operation. Towards the housing (10), it has a shoulder (92), which ends in a circumferential locking bead (94). By means of the shoulder (92), the safety cap (90) sits firmly on the upper end face of the housing (10). The locking bead (94) engages elastically in a groove of the housing (10) in order to fix the cap (90) securely and, if appropriate, sealingly on the housing (10).

FIG. 8 shows the disposable injector with the safety cap (90) removed and with the trigger slide (82) partially actuated, i.e. partially pressed down. By means of this partial actuation, the upper contact zone (18) of the trigger levers (16) is pressed against the slide surface (84) of the catch element (95), see FIG. 7. The contact zone (18) slides along the slide surface (84) towards the centre line (5). The individual trigger lever (16) in each case pivots about a horizontal axis, which lies in the area of the respective foot (25) or in the area of the ring (20).

As a result of the movement of the trigger levers (16), the catch element (95) is pushed upwards out of the hollow space (67). The trigger levers (16) now lie on the support portions (65) of the tension hooks (62). By further depression of the trigger slide (82), the lower contact zone (19) is pressed against the support portion (65). In this way, the tension hooks (62) are bent elastically and/or plastically in the radial direction towards the centre line (5). The support portions (65) are displaced, sliding on the intermediate base, in the direction of the centre line (5). The gap space between the individual tension hooks (62) is substantially used up at least in the area of the support portions (65), see FIG. 9. As soon as the maximum external diameter of the support portions (65) is smaller than the diameter of the bore (34), the tension hooks (62) can move downwards under the effect of the spring element (50) and displace the piston (111) by way of the piston slide (76), see FIG. 10.

FIGS. 12 to 18 show a disposable injector variant in which the trigger levers (16) are formed integrally on the housing (10) and spring elastically towards the centre line (5) of the disposable injector. The housing (10) is essentially a smooth tube with a flat intermediate base (32) located at the top. A central bore (34) for passage of the piston-actuating ram (60) is formed in the intermediate base (32).

The fixing area (41) for receiving the insertable cylinder/piston unit (100) is located in the lower area of the housing (10). The fixing area (41) is slit longitudinally, for example four times, see also FIG. 16. The inner wall of this area has a thread (46) for example. According to FIGS. 10 to 15, the fixing area (41) is surrounded by a support sleeve (49) locked on the housing (10).

A cylinder/piston unit (100) is screwed into the thread (46). It consists of a cylinder (101) and a piston (111). The cylinder (101) is for example a thick-walled pot, of which the optionally cylindrical outer wall also has a thread (104) at least in some areas.

The piston-actuating ram (60) sits between the intermediate base (32) and the cylinder/piston unit (100) in the housing (10). All the areas (61, 73, 75, 76) of the piston-actuating ram (60) are shown at least approximately from FIG. 7.

Here too, the rear end of the housing (10) is closed by means of a safety cap (90). It is substantially comparable to the one in FIG. 7. However, the housing is slit several times in the trigger area (21), see also FIGS. 16 and 17, such that the safety cap (90) is designed extending down as far as the intermediate base.

In this embodiment, four broad trigger levers (16), for example, are used that are formed integrally on the intermediate base (32). The trigger levers (16), see FIG. 17, have crescent-shaped cross sections and each have a central hinge (22), see FIG. 18. This hinge (22) separates the upper contact zone (18) from the lower contact zone (19) and the upper part (27) of the outer contour (17) from the lower part (28) of this contour.

As a bevel at its lower edge, the trigger slide (82) has a broad slide surface (84) which has the shape of a frustoconical jacket surface and whose cone angle measures approximately 12 to 16 angle degrees. This slide surface (84) already lies flat on the upper part (27) of the outer contour (17) in the locked position (8), see FIG. 18. If the trigger slide (82) is now actuated by pressing it, the upper areas (23) of the trigger levers (16) pivot towards the centre line (5) independently of the lower areas (24) of the trigger levers (16), and, via their upper contact zone (18), they force the catch element (95) upwards. The latter springs out of the hollow space (67), see FIG. 13. The upper areas (23) of the trigger levers (16) pivot relative to the lower areas (24) at the elastic hinges (22).

Upon a continuous further movement of the trigger slide (82), the slide surface (84) slips past the zone with the hinges (22) and now forces the lower areas (24) of the trigger levers (16) against the support portions (65) of the tension hooks (62), see FIG. 14. In doing so, the lower areas (24) buckle elastically or plastically on the intermediate base (32), but without tearing off at the intermediate base (32). The support portions (65) push the lower contact zone (19) past the edge (36) into the bore (34). The piston-actuating ram (60) shoots downwards, see FIG. 15.

In this variant, the slide surface (84), the contact zones (18, 19), the outer contour parts (27, 28) and the outer wall (97) can also be spherical surfaces.

Except for the spring elements (50, 64), the apertured disc (39) and the optionally used metal plate (116) of the piston (111), all parts of the disposable injector are made of plastics or of materials similar to plastic or to rubber. Individual areas of plastic subjected to a high degree of loading, for example by Hertzian surface stress, can be plated with ceramic.

LIST OF REFERENCE NUMBERS 1 injection solution; medicament
5 centre line of disposable injector
8 locked position
10 housing, in one piece
11 housing interior
12 housing end face, bottom
16 trigger lever
17 outer contour
18 inner contour, top; contact zone, top
19 inner contour, bottom; contact zone, bottom
20 ring
21 trigger area
22 hinge, film-hinge
23 area, top
24 area, bottom
25 foot
27 outer contour, upper part
28 outer contour, lower part
31 jacket area
32 intermediate base
34 opening, bore, recess
36 housing edge
37 bearing surface
39 apertured disc
41 fixing area for the cylinder/piston unit
42 channels, angular
44 bayonet pin
46 thread, inner thread
49 support sleeve
50 spring element, helical compression spring, spring energy reservoir
60 piston-actuating ram
61 tension bar
62 tension hook
63 envelope surface, bottom
64 spring element, helical compression spring
65 support portion
66 outer contour, envelope surface, top
67 hollow space between the tension hooks
68 envelope surface, inner
69 slits between the tension hooks
73 ram plate
74 grooves
75 portion, e.g. cylindrical
76 piston slide
77 hinge
80 trigger unit
82 trigger slide, press-button, triggering component
83 inner edge
84 slide surface, area
86 trigger wedge
89 recess
90 safety cap
91 base
92 shoulder
94 locking beads, locking lugs
95 catch element, plate-shaped
96 edge
97 outer wall, frustoconical
98 catch pin
99 support surface
100 cylinder/piston unit
101 cylinder
103 end face
104 thread
106 bore, nozzle
107 recess in the end face
111 piston
112 annular groove
114 sealing ring
116 metal plate, magnetic or magnetizable
120 protective film, adhesive seal

What is claimed is:
1. A disposable injector comprising:
a housing (10) in which or on which are arranged, in each case at least in some areas, a mechanical spring energy reservoir (50), the housing (10) having a bearing surface (37) proximate a recess (34) therethrough,
a cylinder and piston unit (100) that can be filled at least temporarily with active substance, the cylinder and piston unit (100) comprising a piston (111) and a cylinder (101),
a piston-actuating ram (60) and a trigger unit (80) in operative arrangement with the cylinder and piston unit (100),
the spring energy reservoir (50) includes at least one pre-tensioned spring element, at least part of the piston-actuating ram (60) is operatively arranged between the spring energy reservoir (50) and the piston (111) of the cylinder and piston unit (100),
the spring-loaded piston-actuating ram (60) includes a tension bar (61) which is transversely movable at least in some areas between a locked active substance pre-dispensing position and an unlocked active substance dispensing position and the tension bar (61) includes a support portion (65), the housing (10) has a housing edge (36) proximate the recess (34), the tension bar (61) forms, together with the support portion (65), a tension hook (62) which, in the locked position, engages over the housing edge (36), the bearing surface (37) of the housing (10) in supportive relationship with the support portion (65), the support portion (65) for supporting the tensioned spring energy reservoir (50) in the locked position, the trigger unit (80) includes a trigger slide (82), a transversely movable trigger lever (16) bearing on the housing (10), and a catch element (95) for holding the tension hook (62) in the locked position, the trigger slide (82) has a conical, frustoconical or pyramidal area (84) and carries in its interior a trigger wedge (86), the tension hook (62), the trigger lever (16), and the catch element (95) are located in the trigger unit (80), the catch element (95) bears on the left-hand side thereof on the trigger wedge (86) and at the right-hand side thereof on an upper contact zone (18) of the trigger lever (16), a part of the catch element (95) simultaneously sits in the recess (34), blocking the tension hook (62) in the locked position, and the trigger slide (82) in operative arrangement with the transversely movable trigger lever (16), the trigger slide (82) for displacing transversely the trigger lever (16) by a longitudinal sliding movement or pivoting movement of the trigger slide (82) for simultaneously pushing the catch element (95) upwardly by forcing the trigger lever (16) inwardly and the trigger wedge (86) simultaneously contacting and releasing the tension hook (62) from the locked position by sliding the support portion (65) from the bearing surface (37) by the trigger wedge (86) pushing the support portion (65) transversely.

2. The disposable injector according to claim 1, further comprising a safety element (90) resting on the bearing surface (37).

* * * * *